(12) United States Patent
Lee et al.

(10) Patent No.: US 6,451,846 B1
(45) Date of Patent: Sep. 17, 2002

(54) ISOCOUMARIN DERIVATIVES INHIBITING ANGIOGENESIS

(75) Inventors: Jung Joon Lee; Hang-Sub Kim; Jeong-Hyung Lee; Young-Soo Hong; Yun Joo Park, all of Taejon-si (KR)

(73) Assignee: Korea Research Institute of Bioscience and Biotechnology (KR)

( * ) Notice: Subject to any disclaimer, the term of this patent is extended or adjusted under 35 U.S.C. 154(b) by 0 days.

(21) Appl. No.: 09/980,904
(22) PCT Filed: Jun. 1, 2000
(86) PCT No.: PCT/KR00/00576
§ 371 (c)(1),
(2), (4) Date: Feb. 26, 2002
(87) PCT Pub. No.: WO00/75124
PCT Pub. Date: Dec. 14, 2000

(30) Foreign Application Priority Data

Jun. 3, 1999 (KR) ............................................. 99/20374

(51) Int. Cl.⁷ ................................................ A61K 31/35
(52) U.S. Cl. ........................................ 514/456; 549/287
(58) Field of Search ........................... 514/456; 549/287

(56) References Cited

U.S. PATENT DOCUMENTS 4,650,881 A    3/1987   Larock et al. ............... 549/290
5,925,671 A    7/1999   Hernandez et al. ......... 514/457
6,020,363 A    2/2000   Hirano et al. ............... 514/456

FOREIGN PATENT DOCUMENTS

EP         0 771 565 A2     7/1997

OTHER PUBLICATIONS

Kimura, et al., *Biosyntheses of Sescandelin B: New Isocoumarin Compounds Produced by the Fungus, Sesquicilium candelabrum*, Biosci. Biotech. Biochem., 58 (8), 1525–1526 (1994).

The Journal of Antibiotics, *Inhibition of Angiogensis by a New Isocoumarin, NM–3*, vol. 52, No. 4, Apr. 1999.

*Primary Examiner*—Amelia Owens
(74) *Attorney, Agent, or Firm*—Roberts & Mercanti, LLP

(57) ABSTRACT

The present invention relates to novel isocoumarin derivatves inhibiting angiogenesis, a method for preparation thereof and pharmaceutical compositions comprising the said derivatives as pharmaceutically active ingredients. More particularly, the present invention relates to novel isocoumarin derivatves represented by formula (1), especially 6,8-dihydroxy-4-acetyl-isocoumarin, a method for preparing 6,8-dihydroxy-4-acetyl-isocoumarin from fungi, and pharmaceutical compositions comprising the compounds and/or 6,8-dihydroxy-4-acetyl-isocoumarin as pharmaceutically active ingredients, which would be effective for the treatment of angiogenic diseases such as cancers, rheumatoid arthritis and diabetic retinopathy.

9 Claims, No Drawings

ISOCOUMARIN DERIVATIVES INHIBITING ANGIOGENESIS

This patent application claims a benefit of priority from Korean Patent Application No. 199-20374 filed Jun. 3, 1999, through PCT Application Serial No. PCT/KR00/000576, the contents of each of which are incorporated herein by reference.

FIELD OF THE INVENTION

The present invention relates to novel isocoumarin derivatives inhibiting angiogenesis, a method for preparation thereof and pharmaceutical compositions comprising the said derivatives as pharmaceutically active ingredients.

More particularly, the present invention relates to novel isocoumarin derivatives represented by formula 1, especially 6,8-dihydroxy-4-acetyl-isocoumarin, a method for preparing 6,8-dihydroxy-4-acetyl-isocoumarin from fungi, and pharmaceutical compositions comprising the compounds and/or 6,8-dihydroxy-4-acetyl-isocoumarin as pharmaceutically active ingredients, which would be effective for the treatment of angiogenic diseases such as cancers, rheumatoid arthritis and diabetic retinopathy <Formula 1>

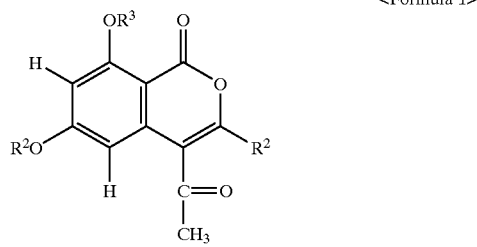

Wherein,
$R^1$ is a hydrogen, alkyl or allylalkyl group; $R^2$ and $R^{3,}$ which may be the same or different, each is hydrogen or an alkyl group.

BACKGROUND

Angiogenesis is a complex process in which capillary blood vessels grow in a complex physiological processes (J. Folkman and M. Klagsbrun et al., *Science*, Vol. 235, pp 442–447, 1987; J. Folkman and Y. Shing, J. et al., *Biol. Chem.*, Vol. 267, pp. 10931–10934, 1992). Angiogenesis is driven by a complex array of, soluble mediators, matrix molecules and accessory cells that function to fine-tune and coordinate the response in both time and space. The initiation of angiogenesis is mediated by multiple molecules that are released from a number of sources including inflammatory cells, such as mast cells and macrophage as well as a variety of tumor cells. These molecules activate the normally quiescent vascular endothelium by binding to their respective receptors. These activated endothelial cells have a characteristic set of traits which include increased cellular proliferation, elevated expression of cell adhesion molecules, increased secretion of proteolytic enzymes, increased cellular migration and invasion, and differentiation to capillary tube. These complex cellular processes should be successfully accomplished to complete angiogenesis.

Angiogenesis is plays important role in a variety of normal physiological events, including trophoblast implantation, wound healing and embryonic development. Uncontrolled angiogenesis, however, can contribute to a number of pathological processes such as rheumatoid arthritis, diabetic retinopathy, and tumor growth and metastasis.

Malignancies are characterized by the growth and spread of tumors. One crucial factor is angiogenesis. Once a tumor has appeared, every increase in tumor cell population must be preceded by an increase in new capillaries that converge on the tumor and supply the cells with oxygen and nutrients (J. Folkman, *Perspect. in Biol. and Med.*, Vol 29, p. 10–36, 1985; N. Weidner, et al., *Amer. J. Pathol.*, Vol. 143, pp. 401–409, 1993). Tumors may thus remain harmless and confined to their tissue of origin, as long as angiogenesis is prevented from being activated. Therefore inhibition of tumor-associated angiogenesis is a most promising approach in cancer therapy (M. S. O'Reilly, et al., *Cell*, Vol. 79, pp. 316–328, 1994).

Many experimental evidence supports the hypothesis that tumor angiogenesis is fundamental for the growth and metastasis of solid tumors (M. S. O'Reilly, et al., ibid. 1994; N. Weidner, et al., *N. Eng. J. Med.*, Vol. 324, pp. 1–8, 1991). Indeed, the majority of solid tumors are not even clinically detectable until after the occurrence of neovascularization, whose induction in solid tumors is mediated by one or more angiogenic factors (J. Folkman and Y. Shing, *J. Biol. Chem.*, Vol. 267, pp. 10931–10934, 1992). Furthermore, angiogenesis is also important in a number of other pathological processes, including arthritis, psoriasis, diabetic retinopathy, and chronic inflammation (J. Folkman, *Nature Medicine*, Vol 1, p. 27–31, 1995; J. W. Miller, et al., *J. Pathol.*, Vol. 145, pp. 574–584, 1994; A. P. Adamid, et al., *Amer. J. Ophthal.*, Vol. 118, pp. 445–450, 1994; K. Takahashi, at al., *J. Clin. Invest.*, Vol.93, pp.2357–2364, 1994; D. J. Peacock, et al., *J. Exp. Med.*, Vol. 175, pp. 1135–1138, 1992; B. J. Nickoloff, et al., *Amer. J. Pathol.*, Vol. 44, pp. 820–828, 1994). Thus, clearly methods of blocking the mechanism of angiogenesis are necessary to treat, so called, angiogenic diseases.

In vitro angiogenesis assays are important for identification of potential angiogenic inhibitors and rapid screening for pharmacological inhibitors. As noted above, differentiation of endothelial cells to capillary-like structure on Matrigel is essential processes for the mechanism of angiogenesis. When endothelial cells are plated on Matrigel, a reconstituted basement membrane protein derived from the Engelbreth-Holm-Swarm mouse tumor, the cells stop proliferating and display high motility and cell-cell communication. Moreover, the cells align and form tubes proposed as models of endothelial cell differentiation, the final step of angiogenesis. These tubes are morphologically similar to capillaries in that the cells that form these tubes are polarized and a central lumen is observed. This in vitro angiogenesis assay is very useful method to evaluate antiangiogenic activity of various compounds.

In order to treat angiogenesis-related diseases, several inhibitors of the above mechanism of angiogenesis are being studied, including platelet factor 4, the fumagillin derivative AGM 1470, Interferon-alpha, thrombospondin, angiostatic steroids, and angiostatin (J. Folkman, et al., ibid., 1995; M. S. O'Reilly, et al., ibid., 1994; V. Castle, et al., *J. Clin. Invest.*, Vol. 87, pp.1183–1888; D. Ingber, et al., *Nature,* Vol. 348, pp. 555–557). All of these compounds have disadvantages. For example, endostatin and angiostatin are proteins, so that they have all of the disadvantages of proteins, including the requirement for being administered parenterally. Therefore, a non-protein inhibitor, which would selectively block the underlying mechanism of angiogenesis without adversely affecting other physiological functions, and which could be administered by many different routes, would be extremely useful. Therefore continuous development of angiogenesis inhibitors having less toxicity and more excellent effect is further required.

Based on the above, the present inventors have performed extensive screening of microbial metabolites to solve the problems described above using in vitro angiogenesis assays, and as a result, discovered 6,8-dihydroxy-4-(1-hydroxyethyl)-isocoumarin and a novel 6,8-dihydroxy-4-acetyl-isocoumarin from a fungal strain of soil. These, two isocoumarin derivatives are highly effective in inhibiting angiogenesis in vitro and in vivo. Finally, the inventors of the present invention found these compounds and their general alkyl or allyl derivatives as therapeutics of angiogenic diseases.

SUMMARY OF THE INVENTION

The invention provides novel isocoumarin derivatives inhibiting angiogensis represented by formula 1, including a method for preparing isocoumarin derivatives.

The invention also provides pharmaceutical compositions comprising isocoumarin derivatives as pharmaceutically active ingredients.

DETAILED DESCRIPTION OF PREFERRED EMBODIMENTS

The present invention provides novel isocoumarin derivatives inhibiting angiogensis represented by the formula 1;

<Formula 1>

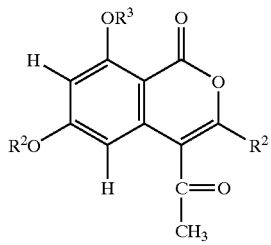

Wherein,

R$^1$ is a hydrogen, alkyl or allylalkyl group; R$^2$ and R$^3$, which may be the same or different, each is hydrogen or an alkyl group.

In addition, the present invention provides 6,8-dihydroxy-4-acetyl-isocoumarin represented by formula 2 as a preferable embodiment of angiogenesis-inhibiting isocoumarin derivatives.

<Formula 2>

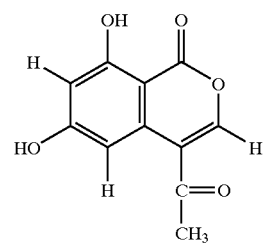

The 6,8-dihydroxy-4-acetyl-isocoumarin can be prepared from fungus, Sesquicllium sp. Y70832, of soil.

The present invention provides a method of purification the active ingredients from a culture broth of the Sesquicillium sp. Y70832 using solvent extraction, column chromatography, and high performance liquid chromatography.

Additionally, the present invention provides pharmaceutical compositions comprising as a pharmaceutically active ingredient the compound of the formula 1, especially 6,8-dihydroxy-4-acetyl-isocoumarin, which is effective for the treatment of angiogenic diseases, such as cancers, rheumatoid arthritis and diabetic retinopathy.

Also, the present invention provides pharmaceutical compositions comprising as a pharmaceutically active ingredient a compound of the following formula 3, which is effective for the medical treatment of angiogenic diseases, such as cancers, rheumatoid arthritis and diabetic retinopathy.

<Formula 3>

The pharmaceutical compositions comprising compounds of the present invention can be administered, in combination with other anti-cancer agents for the treatment of cancer or antiinflammatory drugs for the treatment of rheumatoid arthritis and diabetic retinopathy.

Hereinafter, the present invention is described in detail 6,8-dihydroxy-4-acetyl-isocoumarin represented by the formula 2 is prepared from fungi as follows.

First, Sesquicillium sp. Y70832, which can be isolated from soil, is cultured. The culture is extracted with acetone, concentrated and then extracted again with ethyl acetate. Next, the ethyl acetate extract is purified by silica gel column chromatography using a mixed solvent of methylene chloride and methanol to afford an active fraction. Further purification can be made on the active fraction through Sephadex LH20 column chromatography. From the purified extract, two active ingredients A and B are separated by high performance liquid chromatography using a mixed solvent of acetonitrile and water.

Through instrumental analysis, the structure of active ingredients A and B were identified as 6,8-dihydroxy-4-(1-hydroxyethyl)-isocoumarin of the formula 3 and a novel 6,8-dihydroxy-4-acetyl-isocoumarin of the formula 2, respectively.

6,8-Dihydroxy-4-acetyl-isocoumarin represented by the formula 2, can be converted into the isocoumarin derivatives of the formula 1 by introducing alkyl or alkylallyl group into the carbon of position 3 and/or alkyl ether group into the carbon of positions 6 and/or 8.

In order to determine the inhibitory effect of the isocoumarin derivatives against the angiogenesis, in vitro, endothelial cells, HUVEC (human umbilical vein endothelial cell) are selected. Under a specific culture condition, endothelial cells are migrated and differentiated into capillary tubes. Similar to the angiogenesis in vivo, the tube formation assay may be a good model to determine the influence of the isocoumarin derivatives on angiogenesis.

Various concentrations of the two isocoumarin derivatives are added to endothelial cells to monitor under a microscope whether the isocoumarin derivatives inhibited the differentiation of endothelial cells into capillary tubes. From this experiment, the two isocoumarin derivatives are found to inhibit the angiogenesis in concentration-dependent manners. In detail, 6,8-dihydroxy-4-(1-hydroxyethyl)-isocoumarin shows an effective inhibitory activity against the differentiation of HUVEC into a capillary tube down to the concentration of 4 µg/ml. However, the differentiation of HUVEC into a capillary tube is inhibited by 6,8-dihydroxy-4-acetyl-isocoumarin down to the concentration of as low as 0.2 µg/ml. 6,8-Dihydroxy-4-acetyl-isocoumarin is thus superior in anti-angiogenesis activity to 6,8-dihydroxy-4-(1-hydroxyethyl)-isocoumarin and exhibits no cytotoxicity on HUVEC.

Chorioallantoic membrane (CAM) assay was used to measure whether the two isocoumarin derivatives are effective to inhibit angiogenesis in vivo. Fertilized chick eggs were kept in a humidified incubator at 37° C. After 3 days incubation, egg albumin were removed with hypodermic needle to allow CAM and yolk sac to drop away from the shell membrane. On day 3.5, the shell was punched out and removed to be a circular window and the shell membrane was removed. For testing of angiogenesis inhibition, a pieces of thermanox coverslip was coated with various concentration of the isocoumarin derivatives. The thermanox coverslip was placed on the chorioallantoic membranes at 4.5-day old chick embryo. After 2 days incubation at 37° C., 10% fat emulsion was injected into chorioallantois and observed blood vessel formation during an embryogenesis or development procedure. As a positive control, retinoic acid was used and non-treated coverslip for negative control. When the CAM showed avascular zone to similar degree of retinoic acid treated CAM that had little vessels compared to negative control, the response was scored as positive, and calculated by the percentage of positive eggs to total numbers of tested eggs. 6,8-Dihydroxy-4-(1-hydroxyethyl)-isocoumarin inhibited angiogenesis by 27.3% at a concentration of 1 µg/egg and by 83.3% at concentration of 10 µg/egg. On the other hand, 6,8-dihydroxy-4-acetyl-isocoumarin inhibited angiogenesis by 50.0% at a concentration of 1 µg/egg and by 93.3% at concentration of 10 µg/egg.

From this result, it was found that 6,8-dihydroxy-4-acetyl-isocoumarin is far superior to 6,8-dihydroxy-4-(1-hydroxyethyl)-isocoumarin in inhibition of angiogenesis.

6,8-Dihydroxy-4-(1-hydroxyethyl)-isocoumarin known by the common name sescandelin, was reported to facilitate generation of root (Y. Kimura et al., *Agric. Biol. Chem.*, 54, 2477–2479, 1990), but has not yet been reported as to its inhibitory effect of angiogenesis. In the present invention, 6,8-dihydroxy-4-(1-hydroxyethyl)-isocoumarin is for the first time found to be useful in inhibiting angiogenesis.

Pharmaceutical compositions comprising 6,8-dihydroxy-4-acetyl-isocoumarin of the present invention as a pharmaceutically active ingredient, are useful for inhibiting proliferation, infiltration and metastasis of cancers as well as other angiogenic diseases, such as rheumatoid arthritis, diabetic retinopathy, etc., through its inhibition of angiogenesis.

In addition, a pharmaceutical compositions comprising 6,8-dihydroxy-4-(1-hydroxyethyl)-isocoumarin of the present invention as a pharmaceutically active ingredient, are also useful for inhibiting proliferation, infiltration and metastasis of cancers as well as other angiogenic diseases, such as rheumatoid arthritis, diabetic retinopathy, etc., through its inhibition of angiogenesis.

The compounds of the present invention may be administered via an oral and a parental route with general formulation. They may be used in combination with a variety of other anti-cancer agents, such as doxorubicin, taxol, etopoxide, camptothecin, 5-fluorouracil, methotrexate, or platinum complex compounds to reduce the toxicity of these anti-cancer agents and to potentiate the therapeutic efficiency. These compounds may be also administered in combination with antiinflammatory drugs for rheumatoid arthritis or drugs for diabetic retinopathy.

As mentioned above, the compounds of the present invention may be administered via oral or parental routes with various formulation. They can be formulated along with pharmaceutically acceptable diluents or expedients, such as generally-used fillers, extenders, binders, wetting agents, disintegrating agents, surfactant, etc. Solid formulation for oral administration is tablets, pills, dusting powder, granules and capsules. This solid formulations are prepared by mixing with more than one excipient, for example starches, calcium carbonate, sucrose, lactose and gelatine. Also, lubricants, such as magnesium stearate is used besides simple excipients. Liquid formulations for oral administration are suspensions, solutions, emulsions and syrups. The above-mentioned formulations can contain various excipients, such as wetting agents, sweeteners, aromatics and preservatives in addition to generally-used simple diluents, such as water and liquid paraffin. Formulations for perenteral administration are sterilized. aqueous solutions, water-insoluble excipients, suspensions, emulsions, freezing-drier and suppositories. Water-insoluble excipients and emulsions can contain propylene glycol, polyethylene glycols, vegetable oil, such as olive oil and injectable ester such as ethyoleate. Suppositories can contain witepsol, microgoal, tween 61, cacao fat, laurine fat and glycerolgelatin.

The dosage units can contain, for example, 1, 2, 3 or 4 individual doses or ½, ⅓ or ¼ of an individual dose. An individual dose preferably contains the amount of active compound which is administered in one application and which usually corresponds to a whole, one half, one third or a quarter of a daily dose.

Effective amount of the present invention is about 1 to 50, preferably 5 to 20 mg/kg of body weight and 1 to 3 times a day can be administered.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation Purification and Structural Analysis of Isocoumarin Derivatives

1) Isolation and Purification of Isocoumarin Derivatives

Sesquicillium sp. Y70382 isolated from soil cultured at 28° C. for 8 days in 6 liters of culture medium containing 2.0% glucose, 0.2% yeast extract, 0.5% polypeptone, 0.05% magnesium sulfate, and 0.1% $KH_2PO_4$. The culture was extracted with 6 liters of acetone, concentrated and re-extracted with ethyl acetate. The ethyl acetate extract thus obtained was separated by silica gel column chromatography using a mixed solvent of methylene chloride and methanol (20:1) to afford an active fraction. After being further purified by Sephadex LH20 column chromatography using methanol, the active fraction was identified to consist of two active ingredients A (162 mg) and B (17 mg) as separated by high performance liquid chromatography (HPLC) using 50% acetonitrile.

2) Structural Analysis of Isocoumarin Derivatives

The structures of the active ingredients A and B, were determined by spectroscopic analyses using nuclear magnetic resonance spectroscopy (Unity 300 MHz, Varian), mass spectroscopy (electron ionization source mass analyzer, Hewlett Packard 59890) and UV-visible light spectroscopy (spectronic array, Milton Roy 3000, methanol solvent). The results of the instrumental analyses are shown in Table 1.

100 $\mu$g/ml heparin) at a density of $2\times10^4$ cells/well. The two compounds obtained in Example 1 were independently added at various concentrations into the wells and the plate was incubated for 18–48 hours in a $CO_2$ incubator. The formation of capillary-like tube was monitored under a microscope during the incubation. The cells in the well containing vehicle (DMSO) became to be robuster and longer hollow tube networks as incubation time went on, but the tubes in the wells containing samples were broken and shortened. The inhibitory activity against tube formation was compared with control by measuring the length of the capillary tubes formed. The results are shown in Table 2, below.

TABLE 1

Instrumental analysis for isocoumarin derivatives

| | carbon position | 6,8-dihydroxy-4-(1-hydroxyethyl)-isocoumarin | | 6,8-dihydroxy-4-acetyl-isocoumarin | |
|---|---|---|---|---|---|
| | | $^1$H NMR | $^{13}$CMR | $^1$H NMR | $^{13}$CMR |
| nuclear magnetic resonance | 1 | | 167.5 | | 166.2 |
| | 3 | 7.36 br s | 142.7 | 8.57 s | 155.0 |
| | 4 | | 123.4 | | 116.6 |
| | 4a | | 138.9 | | 134.9 |
| | 5 | 6.61 d (2.1) | 102.4 | 7.58 d (3.0) | 102.5 |
| | 6 | | 107.2 | | 163.5 |
| | 7 | 6.37 d (2.1) | 103.0 | 6.40 d (2.4) | 103.9 |
| | 8 | | 165.5 | | 163.0 |
| | 8a | | 100.3 | | 98.2 |
| | 9 | 4.82 q (6.3) | 65.2 | | 196.2 |
| | 10 | 1.50 d (6.3) | 23.2 | | 28.3 |
| | 6-OH | | | | |
| | 8-OH | | | 11.0 br | |
| mass analysis m/z (%) | | 222 (100) | | 220 (100) | |
| | | 204 (32) | | 192 (73) | |
| | | 193 (37) | | 177 (42) | |
| | | 179 (60) | | 150 (47) | |
| | | 176 (71) | | | |
| ultraviolet-visible ray spectrom $\lambda_{max}$, nm | | 244 (1.757) | | 229 (2.083) | |
| | | 327 (0.247) | | 263 (1.319) | |
| | | | | 329 (0.341) | |
| molecular formular | | $C_{11}H_{10}O_5$ | | $C_{11}H_8O_6$ | |

From the result, the structures of ingredients A and mined as 6,8-dihydroxy-4-(1-hydroxyethyl)-isocoumarin and 6,8-dihydroxy-4-acetyl-isocoumarin, represented by the formulas 3 and 2, respectively.

Experiment 1

Inhibition of Tube Formation in Human Endothelial Cells

To determine the inhibitory effect of the two compounds obtained in Example 1 on the angiogenesis in vitro, human umbilical vein endothelial cells (HUVEC) were used as a model on the basis that they are migrated and differentiated into capillary tubes on Matrigel HUVEC was cultured in a gelatin-coated culture flask with an M199 medium supplemented with 20% FBS, 2 ng/ml bFGF and 100 $\mu$g/ml heparin at 37° C. incubator in a humidified atmosphere containing 5% $CO_2$. The cultured HUVEC were treated with trypsin/EDTA to make a single cell suspension, the cells were plated on Matrigel coated 96-well plates with an M199 medium supplemented with 20% FBS, 2 ng/ml bFGF and

TABLE 2

Inhibitory activity against angiogenesis in vitro

| 6,8-dihydroxy-4-(1-hydroxyetyl)-isocoumarin ($\mu$g/ml) | Inhibitory activity (%) | 6,8-dihydroxy-4-acetyl-isocoumarin ($\mu$g/ml) | Inhibitory activity (%) |
|---|---|---|---|
| Control (0) | 0 | Control (0) | 0 |
| 0.5 | 0 | 0.05 | 0 |
| 1.0 | 0 | 0.2 | 50 |
| 4 | 60 | 0.5 | 85 |
| 10 | 100 | 1.0 | 100 |

As indicated in Table 2, 6,8-dihydroxy-4-(1-hydroxyethyl)-isocoumarin exhibited inhibitory effect against the differentiation of HUVEC into capillary tubes on Matrigel until its concentration decreased down to 4 $\mu$g/ml. As low as 0.2 $\mu$g/ml of 6,8-dihydroxy-4-acetyl-isocoumarin was still effective in inhibiting differentiation of HUVEC into capillary tubes. 6,8-Dihydroxy-4-acetyl-isocoumarin is thus superior in angiogenesis inhibition to 6,8-dihydroxy-4-(1-hydroxyethyl)-isocoumarin. In addition, the two compounds did not show cytotoxicity to HUVEC at the same concentrations as in the angiogenesis inhibition.

Experiment 2

Inhibition of Angiogenesis in vivo

Chorioallantoic membrane (CAM) assay was used to measure whether the two compounds obtained in Example 1 are effective to inhibit angiogenesis in vivo. Fertilized chick eggs were kept in a humidified incubator at 37° C. After 3 days incubation, about 2 ml of egg albumin were removed with hypodermic needle to allow CAM and yolk sac to drop away from the shell membrane. On day 3.5, the shell was punched out and removed to be a circular window and the shell membrane was removed. For testing of angiogenesis inhibition, a pieces of thermanox coverslip was coated with the isocoumarin derivatives dissolved in ethanol at concentration of 1, 5 and 10 µg/coverslip and the ethanol was evaporated. The thermanox coverslip were placed on the chorioallantoic membranes at 4.5-day old chick embryo. After 2 days incubation at 37° C., 1–2 ml of 10% fat emulsion was injected into chorioallantois and observed blood vessel formation during an embryogenesis or development procedure under a microscope. As a positive control, 1 µg/egg of retinoic acid was used and a negative control was non-treated. coverslip. When the CAM showed avascular zone to similar degree of retinoic acid treated CAM that had little vessels compared to negative control, the response was scored as positive, and calculated by the percentage of positive eggs to total numbers of tested eggs. The results are given in Table 3, below.

TABLE 3

| Inhibition of angiogenesis in vivo | | |
|---|---|---|
| Compound | Concentration (µg/egg) | Inhibition rate (%) |
| Negative control | 0 | 15 |
| Positive control (retinoic acid) | 1 | 79.2 |
| 6,8-dihydroxy-4-(1-hydroxyetyl)-isocoumarin | 1 | 27.3 |
|  | 5 | 66.7 |
|  | 10 | 78.6 |
| 6,8-dihydroxy-4-acetyl-isocoumarin | 1 | 50.0 |
|  | 5 | 83.3 |
|  | 10 | 93.3 | a. the number of anti-angiogenesis positive eggs/the number of used eggs × 100%

As indicated in Table 3, 6,8-dihydroxy-4-(1-hydroxyethyl)-isocoumarin inhibited angiogenesis by 27.3% at a concentration of 1 µg/egg and by 83.3% at concentration of 10 µg/egg. On the other hand, 6,8-dihydroxy-4-acetyl-isocoumarin inhibited angiogenesis by 50.0% at a concentration of 1 µg/egg and by 93.3% at concentration of 10 µg/egg.

From this result, it was found that 6,8-dihydroxy-4-acetyl-isocoumarin is far superior to 6,8-dihydroxy-4-(1-hydroxyethyl)-isocoumarin in inhibition of angiogenesis.

Experiment 3

Acute Toxicity Test with Rat

Specific pathogen-free (SPF) SD-rats (six weeks old) were used for the test of acute toxicity. Suspensions of the compounds of formulae 2 and 3 in 0.5% methyl cellulose were orally administered once at a dose of 300 mg/kg/10 ml to the rats. After the administration, the animals were observed as to their death, clinical symptoms and weight change, and serological and serobiochemically tested. An autopsy was made over the rats with the naked eye to observe whether their abdominal and thoracic organs were damaged. Neither sudden death nor noticeable clinical symptoms were detected from all of the animals administered with the compounds of interest. In addition, no toxic signs were observed in weight change, serologic test, serobiochemical test, and corpse examination. The compounds tested caused no toxic changes rats over the rats to the dose of 300 mg/lkg and thus, found to be safe compounds with a lethal dose ($LD_{50}$) of at least 300 mg/kg when being administered via an oral route.

INDUSTRIAL APPLICABILITY

Isocoumarin derivatives, represented by the formula 1, especially 6,8-dihydroxy-4-acetyl-isocoumarin and 6,8-dihydroxy-4-(1-hydroxyethyl)-isocoumarin are so effective in the inhibition of angiogenesis that they can be used for treatment of angiogenic diseases, including cancers, rheumatoid arthritis and diabetic retinopathy.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:
1. A compound of formula 1:
Formula 1

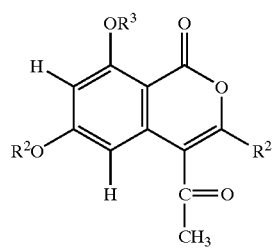

<Formula 1> wherein,
 $R^1$ is a hydrogen, alkyl or allyalkyl group; and
 $R^2$ and $R^3$, which are independently hydrogen or an alkyl group.
2. A compound of claim 1, which is a 6,8-dihydroxy-4-acetyl-isocoumarin derivative represented by the following formula 2:

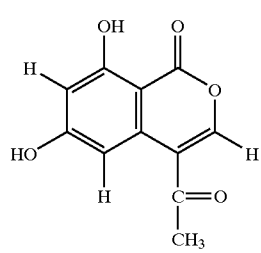

Formula 2

3. The composition of claim 2, which is isolated from Sesquicillium sp. Y70832.
4. A pharmaceutical composition comprising the compound of claim 1.

5. A pharmaceutical composition comprising the compound of claim 2.

6. A method of treating angiogenic diseases, comprising administering an effective amount of a compound of claim 1.

7. The method of claim 6, wherein said angiogenic disease is selected from the group comprising cancers, rheumatoid arthritis and diabetic retinopathy.

8. The method of claim 6, further comprising administering a member of the group consisting of doxorubicin, taxol, eptopoxide, camptothecin, 5-flourouracil, methotrexate and platinum complex compounds.

9. The method of claim 8, further comprising administering an anti-inflammatory drug.

* * * * *